US008485188B2

(12) United States Patent
Nasir

(10) Patent No.: US 8,485,188 B2
(45) Date of Patent: *Jul. 16, 2013

(54) AIRWAY DEVICE

(76) Inventor: Muhammed Aslam Nasir, Luton (GB)

( * ) Notice: Subject to any disclaimer, the term of this patent is extended or adjusted under 35 U.S.C. 154(b) by 142 days.

This patent is subject to a terminal disclaimer.

(21) Appl. No.: 12/859,169

(22) Filed: Aug. 18, 2010

(65) Prior Publication Data

US 2010/0319704 A1 Dec. 23, 2010

Related U.S. Application Data

(62) Division of application No. 10/568,362, filed as application No. PCT/GB2004/003481 on Aug. 13, 2004, now Pat. No. 7,806,119.

(30) Foreign Application Priority Data

Aug. 14, 2003 (GB) .................................. 0319133.5

(51) Int. Cl.
*A61M 11/00* (2006.01)
(52) U.S. Cl.
USPC ................................ 128/205.25; 128/207.15
(58) Field of Classification Search
USPC ............. 128/205.25, 207.15, 206.26, 207.14, 128/207.16
See application file for complete search history.

(56) References Cited

U.S. PATENT DOCUMENTS

| 2,099,127 | A | 11/1937 | Leech | 128/207.15 |
| 3,616,799 | A | 11/1971 | Sparks | 128/351 |
| 3,734,100 | A | 5/1973 | Walker et al. | 128/351 |
| 3,968,800 | A | 7/1976 | Vilasi | 128/343 |
| 3,995,643 | A | 12/1976 | Merav | 128/351 |
| 4,509,514 | A | 4/1985 | Brain | 128/207.15 |
| 4,995,388 | A | 2/1991 | Brain | 128/207.15 |
| 5,174,283 | A | 12/1992 | Parker | 128/200.26 |
| 5,241,956 | A | 9/1993 | Brain | 128/207.15 |
| 5,249,571 | A | 10/1993 | Brain | 128/207.14 |
| 5,282,464 | A | 2/1994 | Brain | 128/207.15 |
| 5,285,778 | A | 2/1994 | Mackin | 128/207.15 |

(Continued)

FOREIGN PATENT DOCUMENTS

| CA | 1324551 | 11/1993 |
| CA | 2 191 749 | 12/1995 |

(Continued)

OTHER PUBLICATIONS

"The Development of the Laryngeal Mask—A Brief History of the invention, Early Clinical Studies and Experimental Work from which the Laryngeal Mask Evolved", A.I.J. Brain, European Journal of Anesthesiology, 1991, Supp. 4., pp. 5-17.

(Continued)

*Primary Examiner* — Steven Douglas
(74) *Attorney, Agent, or Firm* — Hayes Soloway P.C.

(57) ABSTRACT

An airway device for human or animal use comprising an airway tube having a distal end and a proximal end, the distal end of which is surrounded by a laryngeal cuff, wherein the cuff is non-inflatable and is pre-formed in a shape such that a face region of the cuff is adapted to fit snugly over the laryngeal inlet of a patient, and wherein the external profile of the tube is substantially uniform between the distal end of the tube where it starts to meet the cuff and the proximal end of the tube, and wherein the face region of the cuff is formed from a material with a Shore hardness on the A scale of between 0 to 30.

24 Claims, 10 Drawing Sheets

U.S. PATENT DOCUMENTS

| | | | | |
|---|---|---|---|---|
| 5,297,547 | A | 3/1994 | Brain | 128/207.15 |
| 5,303,697 | A | 4/1994 | Brain | 128/200.26 |
| 5,305,743 | A | 4/1994 | Brain | 128/207.15 |
| 5,322,062 | A | 6/1994 | Servas | 128/207.14 |
| 5,355,879 | A | 10/1994 | Brain | 128/207.15 |
| 5,391,248 | A | 2/1995 | Brain | 156/242 |
| 5,477,851 | A | 12/1995 | Callaghan et al. | 128/207.15 |
| 5,584,290 | A | 12/1996 | Brain | 128/207.15 |
| 5,623,921 | A | 4/1997 | Kinsinger et al. | 128/200.26 |
| 5,632,271 | A | 5/1997 | Brain | 128/207.15 |
| 5,655,519 | A | 8/1997 | Alfery | 128/200.26 |
| 5,682,880 | A | 11/1997 | Brain | 128/207.15 |
| 5,711,293 | A | 1/1998 | Brain | 128/200.24 |
| 5,791,341 | A | 8/1998 | Bullard | 128/207.15 |
| 5,865,176 | A | 2/1999 | O'Neil | 128/207.15 |
| 5,878,745 | A | 3/1999 | Brain | 128/207.15 |
| 5,881,726 | A | 3/1999 | Neame | 128/207.15 |
| 5,896,858 | A | 4/1999 | Brain | 128/207.15 |
| 5,915,383 | A | 6/1999 | Pagan | 128/207.15 |
| 5,921,988 | A | 7/1999 | Legrand | 606/87 |
| 5,937,859 | A | 8/1999 | Augustine et al. | 128/207.15 |
| 5,937,860 | A | 8/1999 | Cook | 128/207.15 |
| 5,964,217 | A | 10/1999 | Christopher | 128/200.26 |
| 5,976,072 | A | 11/1999 | Greenberg | 600/120 |
| 5,979,445 | A | 11/1999 | Neame et al. | 128/207.15 |
| 5,988,167 | A | 11/1999 | Kamen | 128 |
| 6,003,514 | A | 12/1999 | Pagan | 128/207.15 |
| 6,055,984 | A | 5/2000 | Brain | 128/207.14 |
| 6,070,581 | A | 6/2000 | Augustine et al. | |
| 6,079,409 | A | 6/2000 | Brain | 128/200.26 |
| D429,811 | S | 8/2000 | Bermudez | D24/110 |
| 6,095,144 | A | 8/2000 | Pagan | 128/207 |
| 6,152,136 | A | 11/2000 | Pagan | 128/207.15 |
| 6,216,696 | B1 | 4/2001 | van den Berg | 128/207.14 |
| 6,280,675 | B1 | 8/2001 | Legrand | 264/262 |
| 6,318,367 | B1 | 11/2001 | Mongeon | 128/207.15 |
| 6,439,232 | B1 | 8/2002 | Brain | 128/207.15 |
| 6,474,332 | B2 | 11/2002 | Arndt | 128/200.26 |
| 6,536,437 | B1 | 3/2003 | Dragisic | 128/207.18 |
| 6,604,525 | B2 | 8/2003 | Pagan | 128/207.15 |
| 6,631,720 | B1 | 10/2003 | Brain | 128/207 |
| 6,679,263 | B2 | 1/2004 | Luchetti et al. | 128/207.15 |
| 6,698,430 | B2 | 3/2004 | Van Landuyt | 128/207.15 |
| 6,705,318 | B1 | 3/2004 | Brain | 128/207.14 |
| 6,792,948 | B2 | 9/2004 | Brain | 128/207.14 |
| 6,799,574 | B1 | 10/2004 | Collins | 128/207.15 |
| 6,877,512 | B2 | 4/2005 | Imai et al. | 128/207.15 |
| 6,918,388 | B2 | 7/2005 | Brain | 128/200.26 |
| 6,918,391 | B1 | 7/2005 | Moore | 128/842 |
| 7,004,169 | B2 | 2/2006 | Brain | 128/207.14 |
| D518,572 | S | 4/2006 | Nasir | D24/110.5 |
| D518,890 | S | 4/2006 | Nasir | D24/110.5 |
| 7,040,312 | B2 | 5/2006 | Alfery et al. | 128/200.26 |
| 7,047,973 | B2 | 5/2006 | Chang | 128/207.15 |
| 7,096,868 | B2 | 8/2006 | Tateo et al. | 128/207.15 |
| 7,134,431 | B2 | 11/2006 | Brain | 128/200.26 |
| 7,140,368 | B1 | 11/2006 | Collins | 128/207.14 |
| 7,263,998 | B2 | 9/2007 | Miller | 128/207.15 |
| RE39,938 | E | 12/2007 | Brain | 128/207.15 |
| 7,305,985 | B2 | 12/2007 | Brain | 128/200.26 |
| 7,506,648 | B2 | 3/2009 | Brain | 128/207.15 |
| D611,138 | S | 3/2010 | Nasir | D24/110.5 |
| D615,188 | S | 5/2010 | Nasir | D24/110.5 |
| D618,788 | S | 6/2010 | Dubach | D24/110.5 |
| 7,762,261 | B1 | 7/2010 | Fortuna | 128/207.14 |
| 7,806,119 | B2 | 10/2010 | Nasir | 128/205.25 |
| 7,896,007 | B2 | 3/2011 | Brain | 128/207.15 |
| 2001/0015207 | A1 | 8/2001 | Pagan | 128/207 |
| 2002/0010417 | A1 | 1/2002 | Bertram | 604/96.01 |
| 2002/0010617 | A1 | 1/2002 | Hamaguchi et al. | 405/10 |
| 2002/0078961 | A1 | 6/2002 | Collins | 128/207.15 |
| 2002/0112728 | A1 | 8/2002 | Landuyt | 128/207.15 |
| 2002/0170556 | A1 | 11/2002 | Gaitini | 128/200.14 |
| 2003/0037790 | A1 | 2/2003 | Brain | 128/207.14 |
| 2003/0066532 | A1 | 4/2003 | Gobel | 128/207.15 |
| 2003/0101998 | A1 | 6/2003 | Zocca et al. | 128/207.15 |
| 2003/0136413 | A1 | 7/2003 | Brain et al. | 128/207.15 |
| 2003/0172925 | A1 | 9/2003 | Zocca et al. | 128/202.22 |
| 2003/0172933 | A1 | 9/2003 | Nimmo | 128/207.14 |
| 2004/0020488 | A1 | 2/2004 | Kniewasser | 128/204.18 |
| 2004/0020491 | A1 | 2/2004 | Fortuna | 128/207 |
| 2005/0051173 | A1 | 3/2005 | Brain | 128/207 |
| 2005/0051175 | A1 | 3/2005 | Brain | 128/207.14 |
| 2005/0066975 | A1 | 3/2005 | Brain | 128/207.15 |
| 2005/0081861 | A1 | 4/2005 | Nasir | 128/207.14 |
| 2005/0103345 | A1 | 5/2005 | Brain | 128/207.15 |
| 2006/0081245 | A1 | 4/2006 | Gould | 128/200.26 |
| 2006/0207601 | A1 | 9/2006 | Nasir | 128/207.14 |
| 2008/0142017 | A1 | 6/2008 | Brain | 128/207.15 |
| 2008/0308109 | A1 | 12/2008 | Brain | 128/207.14 |
| 2010/0126512 | A1 | 5/2010 | Nasir | 128/207.14 |

FOREIGN PATENT DOCUMENTS

| | | |
|---|---|---|
| CA | 2 346 248 | 4/2000 |
| CN | 1166138 | 11/1997 |
| CN | 1236326 | 11/1999 |
| CN | 1351509 | 5/2002 |
| DE | 42 33 933 | 4/1993 |
| DE | 43 30 032 | 4/1994 |
| DE | 195 00 550 | 7/1996 |
| DE | 299 02 267 | 7/1999 |
| DE | 201 00 176 | 5/2001 |
| DE | 202 06 692 | 8/2002 |
| EM | 000067210-002 | 8/2003 |
| EM | 000197124-0001/-0002 | 6/2004 |
| EM | 000197124-0003/-0004 | 6/2004 |
| EM | 000197124-0005/-0006 | 6/2004 |
| EM | 000180757-0001 | 7/2004 |
| EM | 000482195-0001/-0002 | 2/2006 |
| EP | 0 277 797 | 8/1988 |
| EP | 0389272 | 9/1990 |
| EP | 0 448 878 | 10/1991 |
| EP | 0 586 717 | 3/1994 |
| EP | 0 794 807 | 9/1997 |
| EP | 0 834 331 | 8/1998 |
| EP | 0 857 492 | 8/1998 |
| EP | 0 875 260 | 11/1998 |
| EP | 0 884 061 | 12/1998 |
| EP | 0 935 971 | 1/1999 |
| EP | 0911049 | 4/1999 |
| EP | 1125595 | 8/2001 |
| EP | 000067210-001 | 8/2003 |
| EP | 1 579 885 | 9/2005 |
| EP | 1 875 937 | 1/2008 |
| ES | 1 046 206 | 1/2000 |
| FR | 2.094.264 | 1/1972 |
| FR | 2094264 | 1/1972 |
| FR | 2 690 018 | 10/1993 |
| FR | 2 760 186 | 9/1998 |
| FR | 2 807 307 | 10/2001 |
| FR | 2 827 482 | 1/2003 |
| FR | 2 851 107 | 8/2004 |
| GB | 1 402 255 | 8/1975 |
| GB | 2 113 348 | 8/1983 |
| GB | 2 128 561 | 5/1984 |
| GB | 2 168 256 | 6/1986 |
| GB | 2 249 959 | 5/1992 |
| GB | 2 267 034 | 11/1993 |
| GB | 2 285 765 | 7/1995 |
| GB | 2 317 342 | 3/1998 |
| GB | 2 319 182 | 5/1998 |
| GB | 2 323 292 | 9/1998 |
| GB | 2 326 009 | 12/1998 |
| GB | 2 330 312 | 4/1999 |
| GB | 2 337 020 | 11/1999 |
| GB | 2 359 996 | 9/2001 |
| GB | 2 373 188 | 1/2002 |
| GB | 2 364 644 | 2/2002 |
| GB | 2 393 399 | 3/2004 |
| GB | 2 404 863 | 2/2005 |
| GB | 2 413 963 | 11/2005 |
| GB | 2 465 453 | 5/2010 |
| IE | 922073 | 12/1993 |
| IT | 1224077 | 9/1990 |
| JP | 3-236858 | 10/1991 |
| JP | 6/277286 | 10/1994 |
| JP | 2007-509154 | 4/2007 |

| | | |
|---|---|---|
| TW | 224047 | 11/2004 |
| WO | WO 94/17848 | 8/1994 |
| WO | WO 95/09665 | 4/1995 |
| WO | WO 97/12640 | 4/1997 |
| WO | WO 98/06276 | 2/1998 |
| WO | WO 98/24498 | 6/1998 |
| WO | WO 98/50096 | 11/1998 |
| WO | WO 99/24101 | 5/1999 |
| WO | WO 99/44665 | 9/1999 |
| WO | WO 00/09189 | 2/2000 |
| WO | WO 00/30706 | 2/2000 |
| WO | WO 00/61213 | 10/2000 |
| WO | WO 01/13980 | 3/2001 |
| WO | WO 01/97890 | 12/2001 |
| WO | WO 02/32490 | 4/2002 |
| WO | WO 03/020340 | 3/2003 |
| WO | WO 2004/016308 | 2/2004 |
| WO | WO 2005/016427 | 2/2005 |
| WO | WO 2005/041864 | 5/2005 |

OTHER PUBLICATIONS

PCT International Search Report, dated Jan. 14, 2009 (20 pgs).
Office Action issued in U.S. Appl. No. 29/353,658 dated Aug. 19, 2011 (10 pgs).
International Search Report and Written Opinion issued in Applicant's corresponding UK Patent Application Serial No. GB0817776.8.
International Search Report and Written Opinion issued in corresponding application No. PCT/GB2011/051203, dated Jul. 12, 2011 (14 pgs).
UK Search Report issued in corresponding application No. GB1110775.2, dated Oct. 18, 2011 (8 pgs).
US Official Action dated Feb. 14, 2013, issued in U.S. Appl. No. 29/407,461 (21 pgs).
International Search Report and Written Opinion issued in corresponding application No. PCT/GB2011/051203, dated Dec. 7, 2011 (15 pgs).
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).
Extended European Search Report and Written Opinion issued in corresponding EPO application No. 07019251.3, dated Feb. 1, 2008 (8 pgs).
First Office Action issued in corresponding Chinese application No. 200480023382.4, dated Aug. 22, 2008 (15 pgs).
International Search Report and Written Opinion issued in corresponding PCT application No. PCT/GB2009/051574, dated Jun. 7, 2010 (28 pgs).
Combined Search and Examination Report issued in corresponding application No. GB1019839.8, dated Dec. 1, 2010 (2 pgs).
Combined Search and Examination Report issued in corresponding application No. GB 0418050.1, dated Nov. 29, 2004 (7 pgs).
Examination Report issued in corresponding application No. 09 756 353.0-1257, dated Aug. 17, 2012 (5 pgs).
Further examination as result of telephone conversation with examiner issued in corresponding EPO application No. 03 787 902.0 (1 pg).
Letter from IP Australia regarding third party application for re-examination dated Sep. 21, 2011 involving corresponding application No. 2008207412 (2 pgs).
Invitation to Pay Additional Fees with International Search Report issued in corresponding application No. PCT/GB2004/003481, dated Nov. 12, 2004 (8 pgs).
Notice for Reasons for Rejection issued in corresponding Japanese application No. 2006/523053, dated Nov. 8, 2010, with English translation (4 pgs).
International Search Authority issued in corresponding PCT application PCT/GB03/03577 dated, Dec. 9, 2003 (5 pgs).
International Search Report issued in corresponding PCT application PCT/GB03/03577 dated Aug. 14, 2003 (9 pgs).

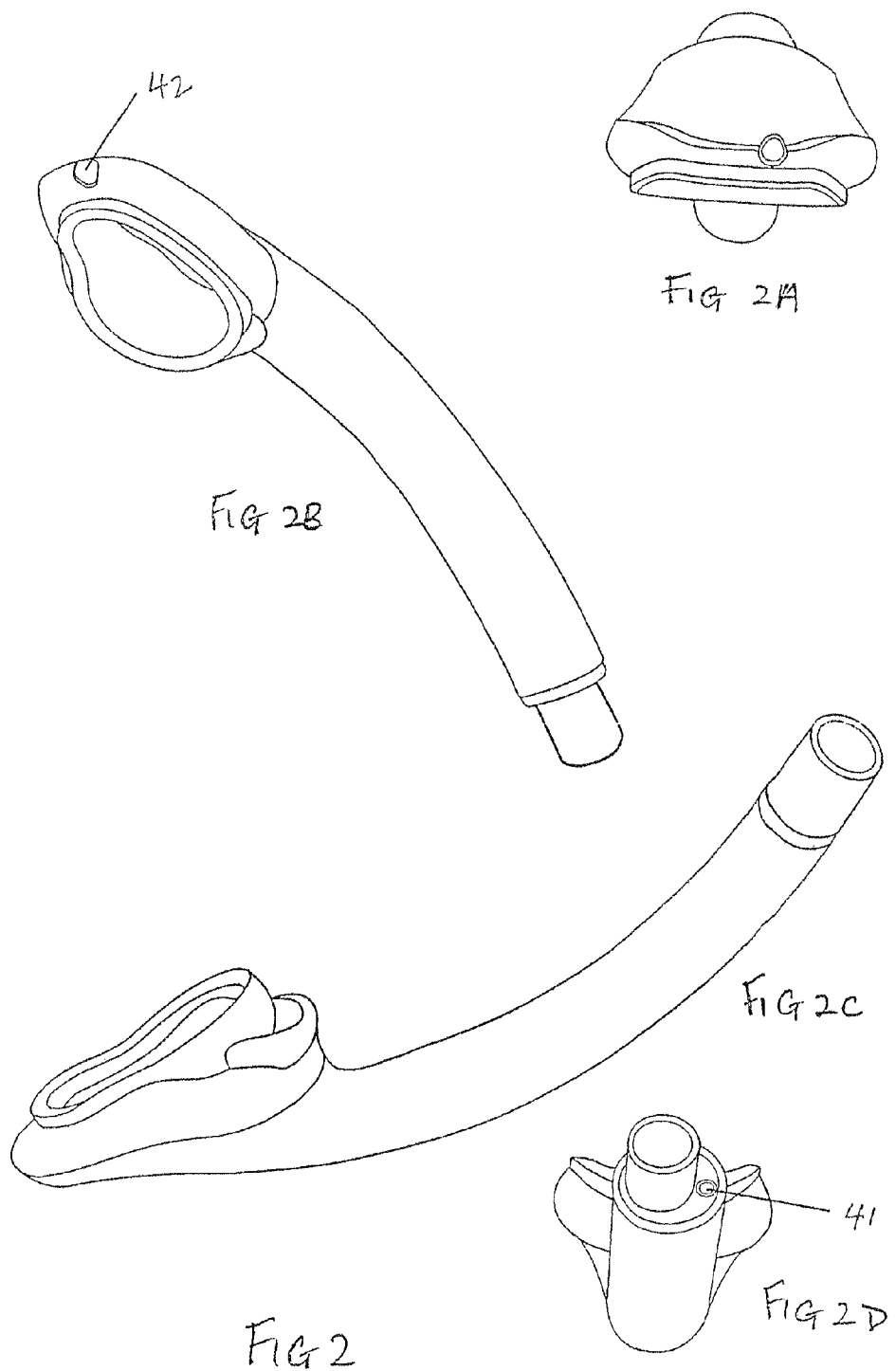

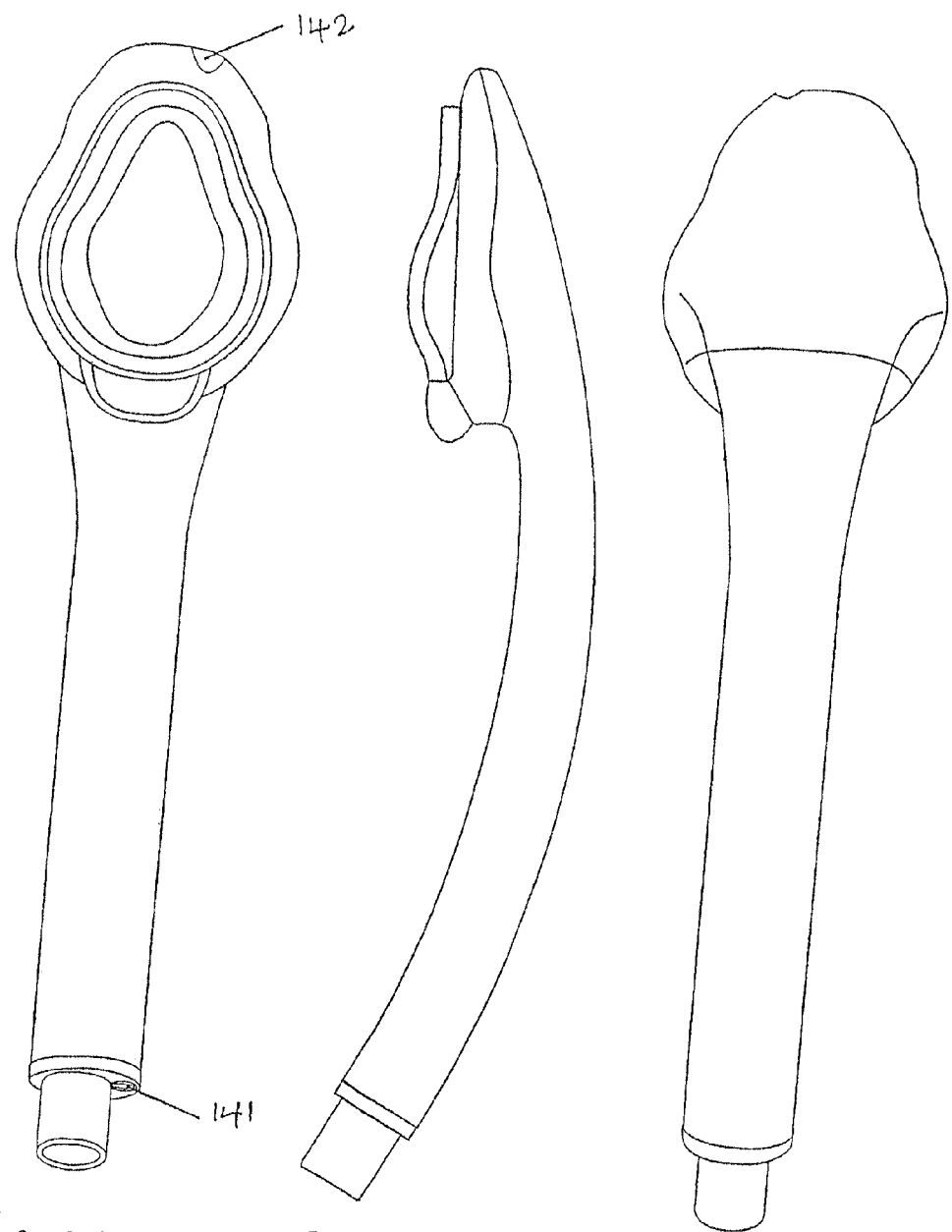

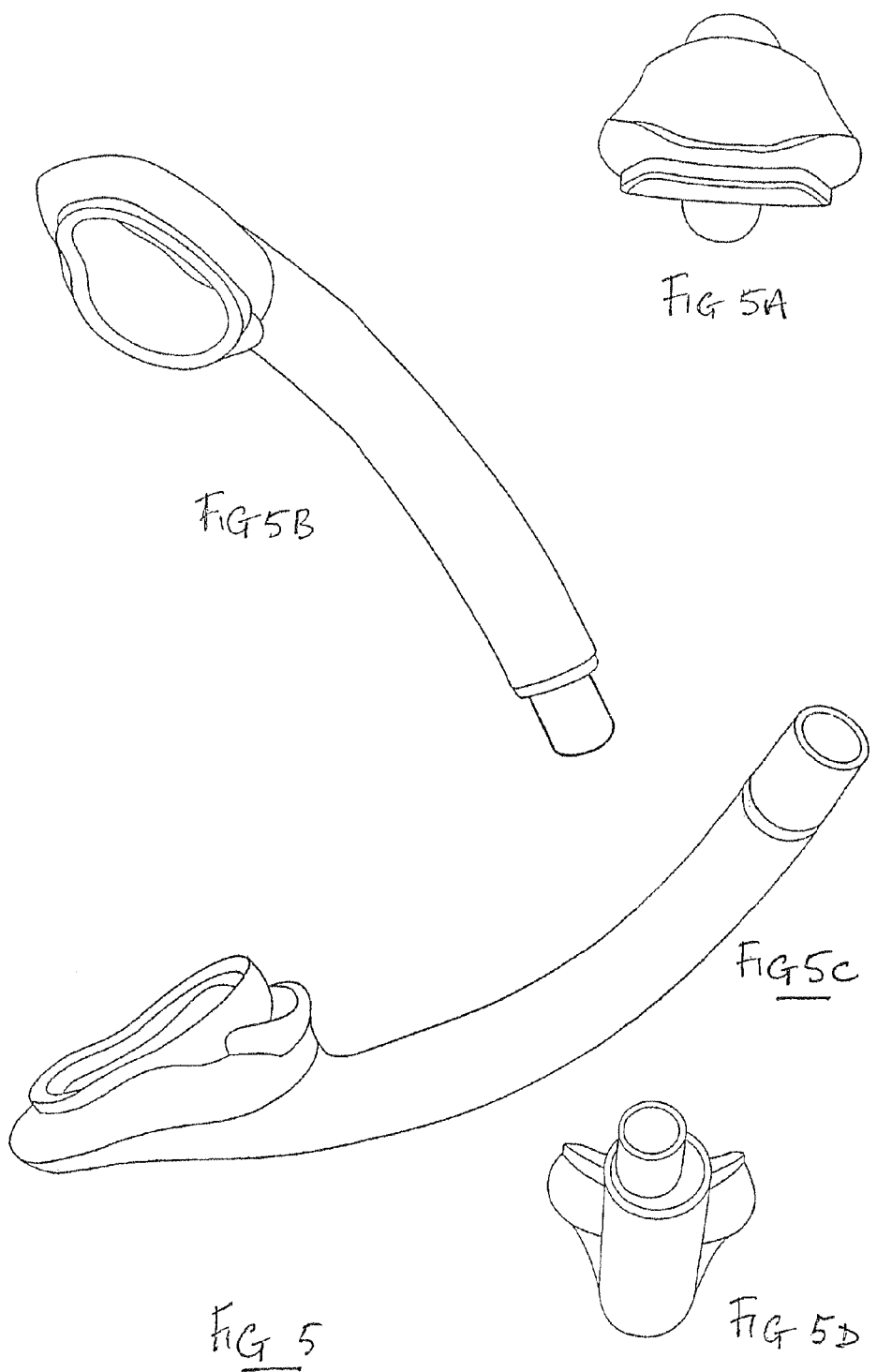

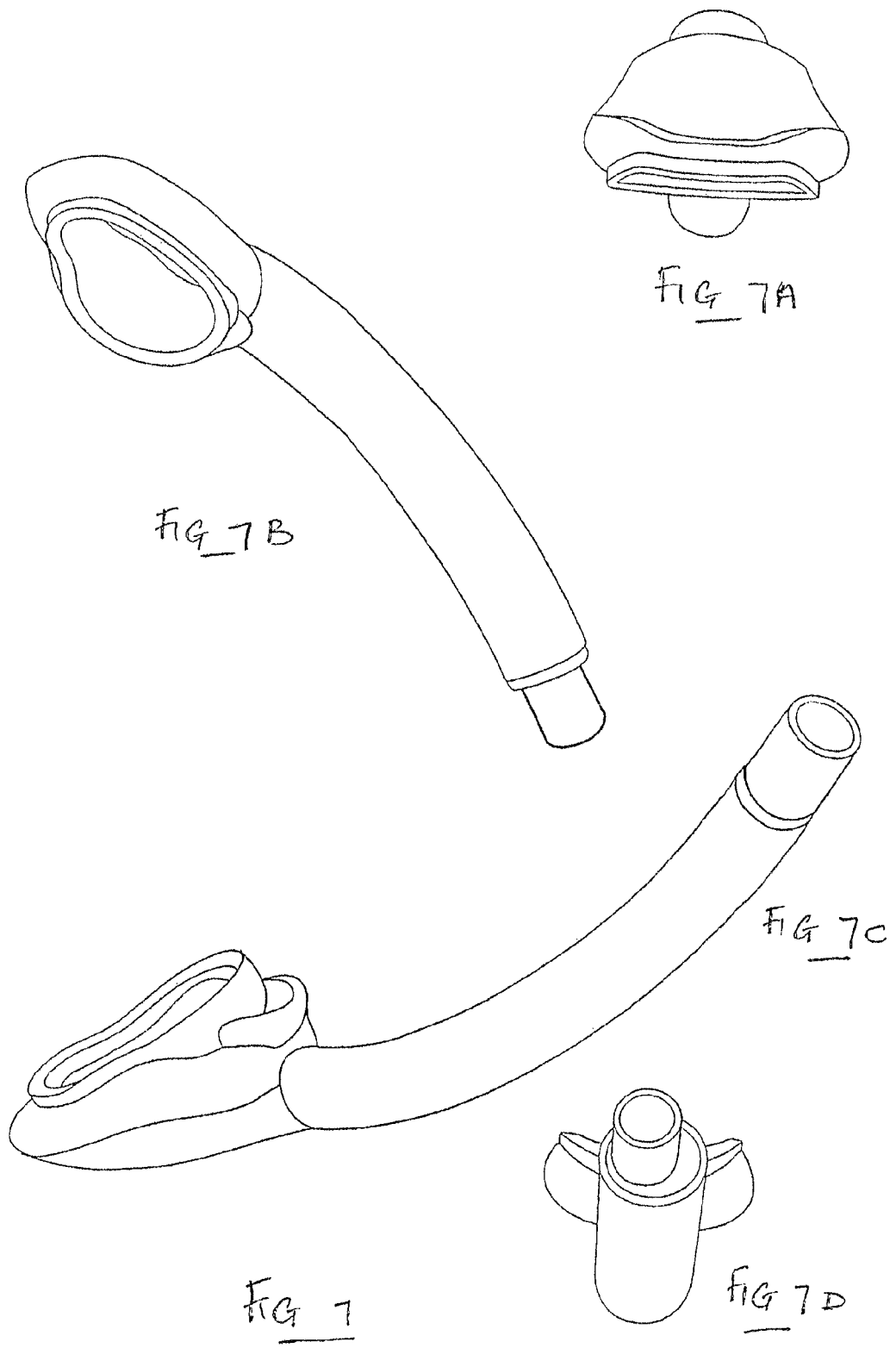

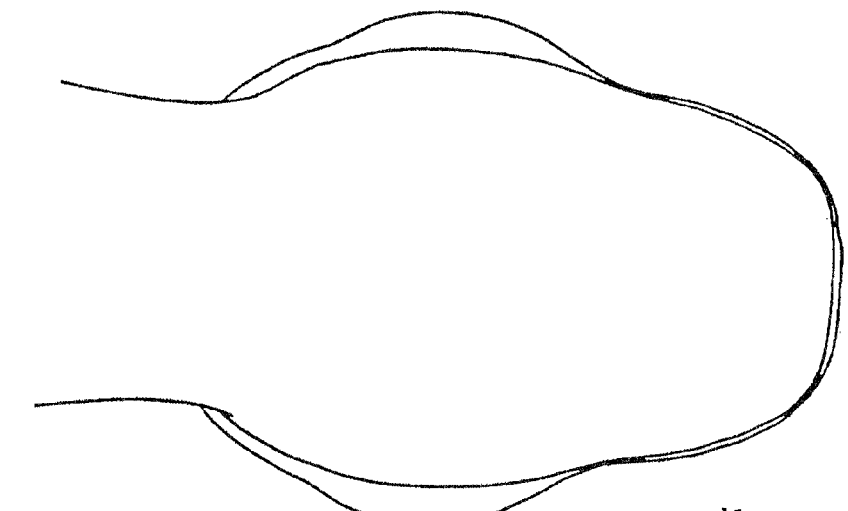
FIG 8A
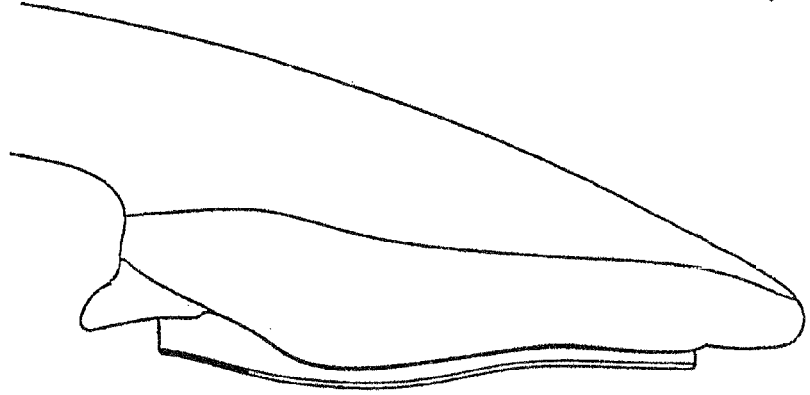
FIG 8B
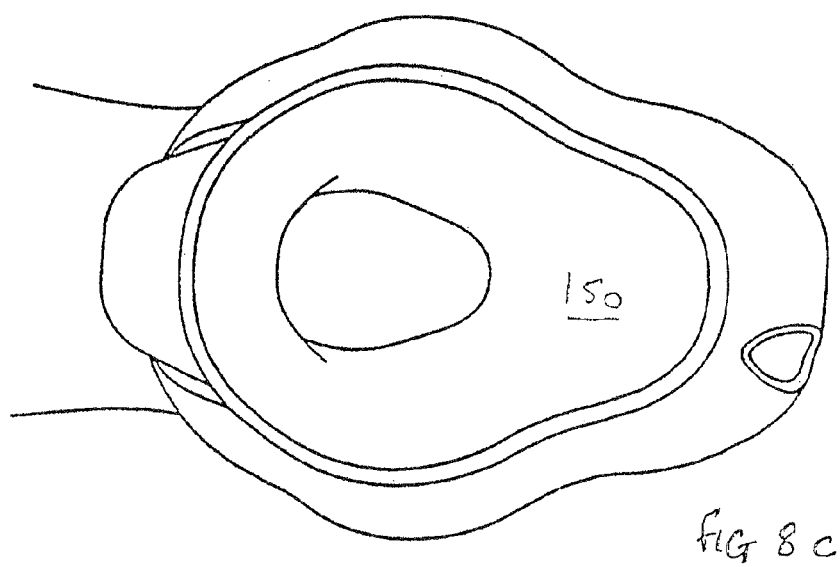
FIG 8
FIG 8C

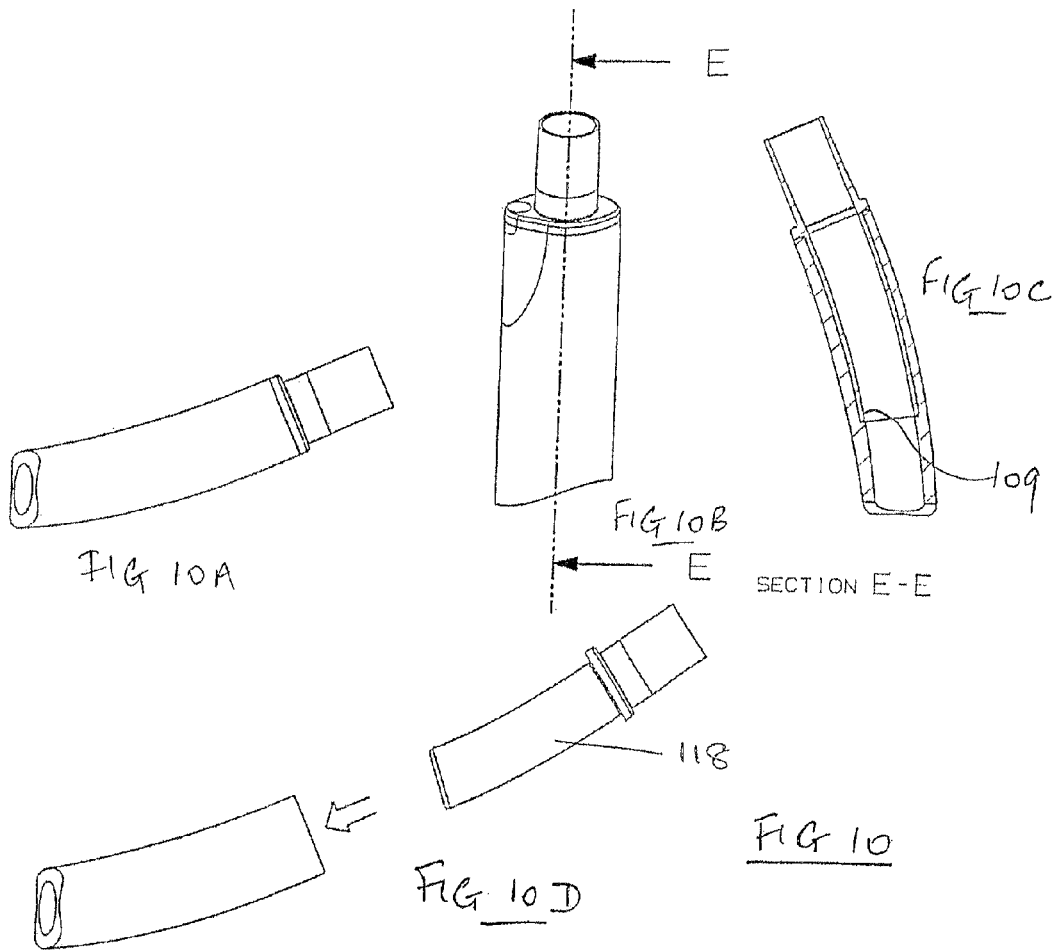
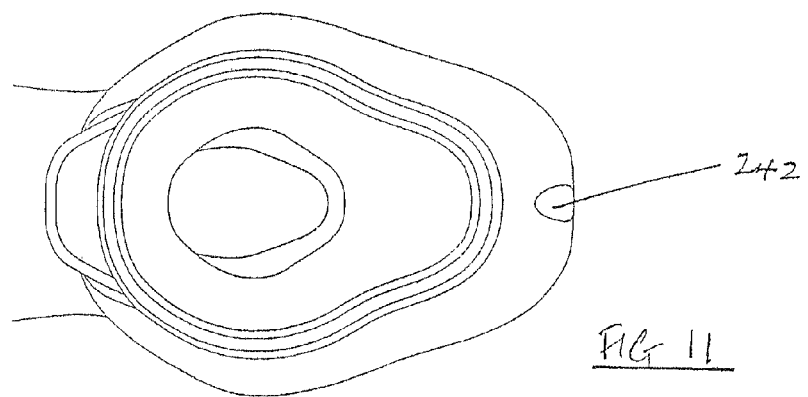

AIRWAY DEVICE

CROSS REFERENCE TO RELATED APPLICATION

This application is a divisional of U.S. application Ser. No. 10/568,362 filed Feb. 14, 2006.

FIELD OF THE INVENTION

The present invention relates to medical devices and is particularly applicable, but in no way limited, to laryngeal airway devices and to their methods of manufacture.

BACKGROUND TO THE INVENTION

A wide variety of devices are known and are currently used in spontaneously breathing anaesthetized patients, during recovering after anesthetics, in weaning of a certain group of patients in intensive care, or during resuscitation to provide a clear and hands-free airway. A number of these devices are listed in the applicant's co-pending earlier application GB2,393,399A (Nasir), the text of which is hereby imported by reference and which is intended to form an integral part of this disclosure. GB2,393,399A describes a new type of airway device which has a soft laryngeal cuff adapted to fit anatomically over and form a seal with the laryngeal structure of a patient. An essential feature of certain embodiments of this device is a so-called buccal cavity stabiliser, located around the airway tube, and which is designed to nest with the anterior aspect of the patient's tongue.

The laryngeal cuffs on these devices are generally non-inflatable, but rather are formed from a soft, deformable material that can adapt to the individual detail of the patient's laryngeal inlet to form a satisfactory seal. It was precisely because of the very soft, deformable nature of these cuffs that it was considered necessary to incorporate some form of stabiliser to locate the cuff during insertion and to maintain a good gas-tight contact with the laryngeal inlet at all times during use. It should be borne in mind that "use" can involve the patient in many hours on the operating table under anaesthesia and can also involve use in accident and emergency situations involving hostile conditions that are non-ideal for such treatments.

It has now unexpectedly been discovered that a stabiliser, whilst still desirable, is not essential to achieve a good gas-tight seal between the cuff and the laryngeal inlet of the patient. Since a buccal cavity stabiliser adds both weight and cost there are positive advantages in eliminating this feature from the design. Weight and cost are both important features, particularly where the item is intended as a single use or disposable item.

It has also been deemed possible to reduce the material in the laryngeal cuff by manufacturing as a preformed/prefilled anatomical cuff, and by potentially removing the gastric channel.

It is an object of the present invention to provide an airway device that is both simple and effective to use and cost-effective to manufacture.

Where a single use item is concerned, cost of manufacture, and minimising this cost, is important. A further objective of the present invention is to provide cost-effective methods for manufacturing airway devices that enable the unit cost per item to be minimised.

It is also an object of this invention to satisfy the requirements of clinical situations where a buccal cavity stabiliser would not enhance, but impede the operation. For example in many opthamalogical, and maxillofacial or dental surgery the use of a reinforced tube are preferable, as the tube can flexibly moved to one side to continue to provide an airway for the patient, whilst not interfering with the operation. In summary, where it might be advantageous to have an airway device with a buccal cavity stabiliser in some applications, we have discovered that there are several applications where this is disadvantageous. In fact there are several applications where it is just not practical to have a buccal cavity stabiliser.

SUMMARY OF THE INVENTION

A first aspect of the present invention provides an airway device as described in the accompanying claims.

Accordingly, according to a first embodiment there is provided an airway device for human or animal use comprising an airway tube having a distal end and a proximal end, the distal end of which is surrounded by a laryngeal cuff, wherein the cuff is non-inflatable and is pre-formed in a shape such that a face region of the cuff is adapted to fit snugly over the laryngeal inlet of a patient, and wherein the external profile of the tube is substantially uniform between the distal end of the tube where it starts to meet the cuff and the proximal end of the tube, and wherein the face region of the cuff is formed from a material with a Shore hardness on the A scale of between 0 to 30.

Such an airway device is both efficient in operation and cost-effective to manufacture.

Preferably the face region of the cuff is formed from a material of Shore hardness on the A scale of between 0 and 20 and more preferably 0 to 5.

Preferably the profile of the airway tube is substantially circular. In an alternative embodiment the profile of the airway tube is substantially elliptical.

Preferably the device further comprises a gastric tube passageway extending from the distal end of the airway tube to the proximal end of the cuff.

Preferably the gastric tube passageway is housed substantially within the body of the device.

Preferably the distal end exit of the gastric tube passageway exits the cuff centrally, that is along the line of the central longitudinal axis of the device.

Alternatively the distal end exit of the gastric tube passageway may be displaced to one side of the central longitudinal axis of the device If the end exit of the gastric tube passageway is displaced it is preferred that the distal end exit of the device is displaced to the right of the central longitudinal axis of the cuff, as viewed from the open face of the cuff, in other words to the right-hand side of the patient when the device is in use. This is for ease of manufacture.

In a particularly preferred embodiment the device further comprises one or more flexible flanges extending around the opening in the face region of the cuff.

Preferably the flexible flanges extend substantially around the entire circumference of the opening in the cuff.

Preferably a plurality of flanges are provided said flanges being spaced apart radially around the opening one from another such that the flanges are substantially concentric.

Advantageously said device further comprises a connector adapted to connect the proximal end of the airway tube to a gas supply.

Preferably said connector extends into said airway tube and at least part way along the length of said airway tube to act as a bite protector to prevent a patient from constricting the airway tube by biting on it.

Preferably said connector fits into an internal annular recess at the proximal end of the airway tube such that the diameter, or internal cross-section of the airway tube where the tube is non-circular internally, remains substantially constant along the length of the tube when the connector is in place.

Preferably the distal end of the connector abuts in use a shoulder in the airway tube to prevent the connector from passing into the airway tube beyond a certain point. This provides a positive fit for the connector which seats on a shoulder or recess within the tube, and results in lower resistance to airflow through the device.

Preferably the face of the laryngeal cuff is adapted to form an anatomical fit over the laryngeal inlet of a patient incorporates protuberances designed to form a good seal with the pyriform fossae and aryepiglottic folds of the laryngeal inlet of the patient.

Preferably the face of the laryngeal cuff adapted to form an anatomical fit over the laryngeal inlet of a patient incorporates protuberances designed to form a good seal with the valleculae, epiglottis, aryepiglottic folds, pyriform fossae and around the anterior aspect of thyroid & cricoid cartilages. The distal tip of the device positions itself into the recess created by the posterior aspect of the lower larynx below the posterior cartilages, above the opening of the esophagus, not only to help create an airway seal but also to act as a physical wedge to prevent the possibility of regurgitation.

Preferably the face of the laryngeal cuff adapted to fit anatomically over the laryngeal framework of a patient incorporates grooves designed to allow passage of vital arteries, veins and nerves supplying the laryngeal framework.

Preferably the distal tip of the laryngeal cup is so sized and shaped as to remain above the upper oesophageal sphincter in use.

Preferably the distal tip of the laryngeal cup is substantially concave in shape.

Preferably the face of the laryngeal cuff and the airway tube are formed from materials of different Shore hardness.

In an alternative embodiment the face of the laryngeal cuff and the airway tube are formed from material of substantially the same Shore hardness.

Preferably the airway tube together with the back or dorsal part of the cuff are made from material of one Shore hardness and the face of the cuff is made from a material of a different Shore hardness, such that the face of the cuff is made of a softer material than the airway tube and the back or dorsal part of the cuff.

According to a further aspect of the invention there is provided a method of manufacturing an airway device suitable for human or animal use, said airway device comprising an airway tube having a distal end and a proximal end, the distal end of which is surrounded by a non-inflatable laryngeal cuff, said method comprising the steps of:
(i) providing a mould, the mould including interior walls defining an interior volume which defines the shape of the airway device;
(ii) introducing a liquid plastics material into the hollow interior volume of the mould;
(iii) optionally introducing a second liquid plastics material into said mould where it is required that the airway device is made from materials of different Shore hardness;
(iv) allowing the plastics material to solidify;
(v) removing the airway device from the mould.

Preferably said method also comprises the step of inserting into said mould a connector suitable for connecting to an anaesthetic gas supply, such that, after the moulding process is complete, the connector becomes attached to the airway device.

According to a further aspect of the invention there is provided a method of manufacturing an airway device suitable for human or animal use, said airway device comprising an airway tube having a distal end and a proximal end, the distal end of which is surrounded by a non-inflatable laryngeal cuff, said method comprising the steps of:—
(i) providing an airway tube;
(ii) providing a mould, said mould including interior walls defining an interior volume which defines the shape of a laryngeal cuff;
(iii) inserting said airway tube into said mould;
(iv) introducing a liquid plastics material into the hollow interior volume of the mould;
(v) optionally introducing a second liquid plastics material into said mould where it is required that the cuff of the airway device is made from materials of different Shore hardness;
(vi) allowing the plastics material to solidify;
(vii) removing the airway device from the mould.

Preferably said airway tube is formed by an extrusion process.

In a still further aspect of the present invention there is provided method of manufacturing an airway device suitable for human or animal use, said airway device comprising an airway tube having a distal end and a proximal end, the distal end of which is surrounded by a non-inflatable laryngeal cuff, said method comprising the steps of:—
(i) providing a mould, the mould including interior walls defining an interior volume which defines the shape of a laryngeal cuff;
(ii) introducing a liquid plastics material into the hollow interior volume of the mould;
(iii) optionally introducing a second liquid plastics material where it is required that the airway device is made from materials of different Shore hardness;
(iv) allowing the plastics material to solidify;
(v) removing the airway device from the mould;
(vi) providing an airway tube;
(vii) bonded said airway tube to said laryngeal cuff.

In a still further aspect of the invention there is provided a method of manufacturing an airway device suitable for human or animal use, said airway device comprising an airway tube having a distal end and a proximal end, the distal end of which is surrounded by a non-inflatable laryngeal cuff, said method comprising the steps of:—
(i) providing an airway tube;
(ii) providing a mould, said mould including interior walls defining an interior volume which defines the shape of a laryngeal cuff and which substantially encapsulates the airway tube;
(iii) inserting said airway tube into said mould;
(iv) introducing a liquid plastics material into the hollow interior volume of the mould, to form the back of the cuff and substantially cover the rigid airway tube
(v) optionally introducing a second liquid plastics material into said mould where it is required that the cuff of the airway device is made from materials of different Shore hardness;
(vi) allowing the plastics material to solidify;
(vii) removing the airway device from the mould.

Preferably said airway tube is formed by an extrusion process.

BRIEF DESCRIPTION OF THE DRAWINGS

The invention will now be described, by way of example only, with reference to the accompanying drawings in which:—

FIGS. 2-2D illustrate various perspective views of the embodiment shown in FIG. 1;

FIGS. 3-3C show front, side and rear elevational views of an airway device according to a second embodiment of the present invention having a substantially elliptical profile airway tube;

FIGS. 5-5D illustrate various perspective views of an embodiment without a gastric tube passageway;

FIGS. 7-7D illustrate various perspective views of the embodiment shown in FIG. 6;

FIGS. 8-8C show enlarged rear, side and front elevational views of a laryngeal cuff;

FIGS. 10-10D illustrate a connector which can also act as a bite protector; and

FIG. 11 illustrates a front elevational view of a laryngeal cuff in which the gastric tube passageway exits on the midline or centrally from the tip of the cuff.

DESCRIPTION OF THE PREFERRED EMBODIMENTS

Embodiments of the present invention are described below by way of example only. These examples represent the best ways of putting the invention into practice that are currently known to the applicant although they are not the only ways in which this could be achieved.

As used herein, the anatomical terms "anterior" and "posterior," with respect to the human body, refer to locations nearer to the front of and to the back of the body, respectively, relative to other locations. In the context of this description, the term "proximal" means the end of the device, or portion thereof, closest to the connection to the anaesthetic breathing system. The term "distal" means the end of the device, or portion thereof, furthest from the anaesthetic breathing system or alternatively, the cuff end of the device. The term "lateral" refers to a location to the right or left sides of the body, relative to other locations. "Bilateral" refers to locations both to the left and right of the body, relative to other locations. The anatomical term "medial" or "medially" refers to a location toward the centre or midline of the body, relative to locations both to the left and right of the body.

Figures 1, 1A, 1B, 1C:
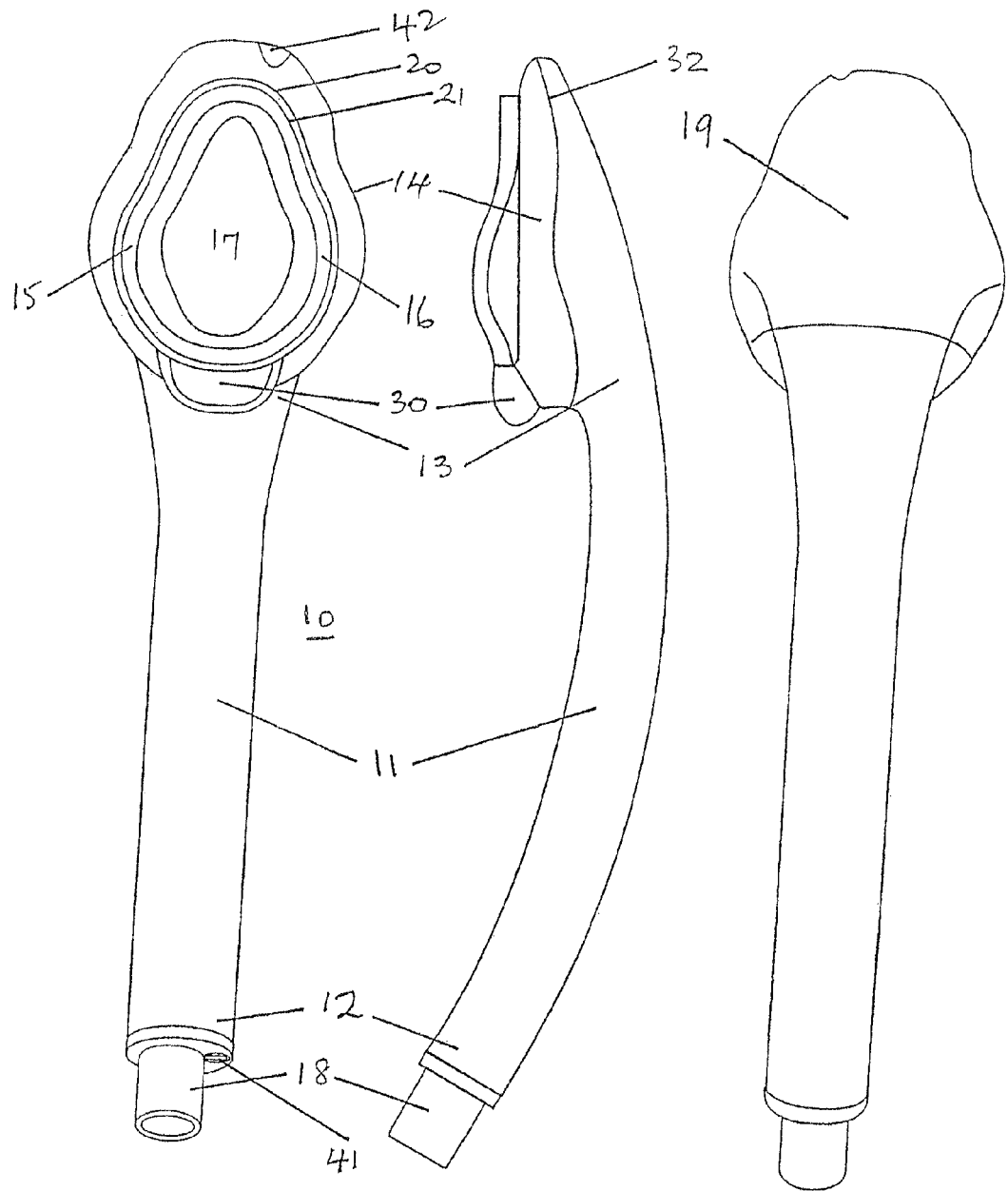
FIGS. 1-1C illustrate front, side and rear elevational views of an airway device according to a first embodiment of the present invention having a substantially circular profile airway tube.

Referring to FIG. 1, this illustrates front, side and rear elevations of an airway device according to a first embodiment of the present invention, generally shown as 10. This comprises an airway tube 11, which at its proximal end 12 terminates in a 15 mm or other connector 18 suitable for connection to an anaesthetic breathing system of conventional type. Formed around the distal end 13 of the airway tube is a laryngeal cuff or cup 14 adapted in its shape and contours to correspond with the laryngeal inlet region of a patient. In this context the terms cuff and cup have an equivalent meaning. They refer to the element of the device at the distal end of the airway tube that is adapted to cover and form a seal with the laryngeal inlet of the patient in use. The anatomy of the laryngeal inlet region of a human is well known to the expert. It is illustrated in some detail in FIG. 1 of GB2,393,399 and the key thereto, both of which are imported herein by reference.

The cuff 14 has an opening 17 in a face or front region of the cuff and the back or dorsal part of the cuff is closed. The opening 17 in the face of the cuff connects directly to the airway tube 11 such that gas is free to flow from the connector 18 through the airway tube and out of the open face of the cuff.

The particular cuff shown in FIG. 1 incorporates in the cuff face pronounced and discernable bulges or protuberances 15, 16 designed to form a good seal with the piriform fossae and aryepiglottic folds. It will be appreciated that the outbulgings in the cuff at 15 and 16 are positioned antero-laterally to the laryngeal framework and give an anatomical seal by fitting into the piriform fossae and aryepiglottic folds and space postero-inferior to the thyroid and cricoid cartilages, and the posterior cartilages (corniculate and cuneiform). Thus, in side elevation, the face of the cuff is not a flat planar surface but includes regions that protrude above the general plane of the cuff face. Additionally, there may optionally be regions which lie below the general plane of the cuff face. These shapings and the general size, shape and configuration of the surface of the cuff face around opening 17 are an important feature of the invention.

Thin, flexible, featherlike flanges 20 and 21 extend substantially around the circumference of the opening 17 in the face region of the cuff. These flanges are preferably formed as an integral part of the moulding of the cuff and, because of the very soft nature of the material used to form the cuff, these flanges are particularly soft and pliable. Their purpose is to make allowance for any individual patient variation in the laryngeal inlet shape and to contribute to forming an efficient and effective seal between the cuff and the laryngeal structures. By this design, and by designing the cuff to be a close anatomical fit, the obtainable seal pressure from experimental trials is well within the range of 12-40 cm $H_2O$, which is sufficient for ventilation.

These flanges need not completely encircle the opening 17 as shown in FIG. 1 but it is preferred that they completely surround the opening circumference, and in doing so they follow the general contours of the front face of the cuff. Flanges 20 and 21 are spaced apart slightly such that each flange is an integral item or unit. The flanges are spaced radially one from another around the opening such that one flange surrounds another. The term "radially" in this context has a broad meaning and refers to the spacing of each flange from an imaginary axis extending out of the opening in a plane substantially perpendicular to the general plane of the cuff face.

In this embodiment two feather flanges are shown. However, there may be no flanges, one flange or two or more than two flanges. In other words there may be none or a plurality of flanges, "plurality" having the meaning one or more in the context of this disclosure.

Figure 9:
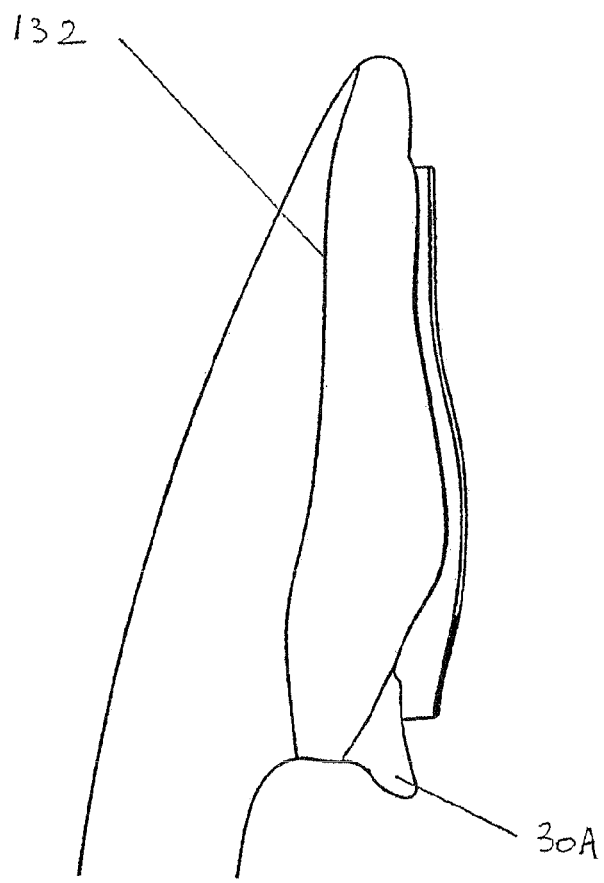
FIG. 9 shows an enlargement of a cuff, detailing the split line between different plastics which would be present if the cuff is to be formed by materials of two different shore hardnesses.

A further feature of the cuff is the epiglottic rest 30 located at the proximal end of the cuff region. This epiglottic rest is sized and shaped so as to be anatomically positioned against the epiglottis, to ensure a proper seal and to hold the epiglottis back from downfolding towards the laryngeal inlet avoiding obstruction to airflow. This epiglottic rest takes the form of a leaf like structure extending out of the laryngeal cuff and directed back towards the proximal end of the airway tube. Its relative size and shape can be seen from 30A in FIG. 9. The optimum size and shape for this epiglottic rest will be determined by experimentation.

Turning now to the airway tube, this is shown generally as 11 in FIG. 1. This tube, which is in the form of a hollow cylinder of substantially uniform cross-section open at each end, extends from the connector end 12 into the body of cuff 14 to connect with cuff opening 17. The inside diameter of the airway tube will depend on the size of the device, generally larger in adult sizes versus pediatric sizes, and designed in general to accommodate the appropriately sized endrotracheal tube for endoscope guided intubation where necessary. The internal diameter of the tube may be substantially uniform along its length, although the internal diameter may vary.

In terms of intubation the airway also has significant benefits over inflatable laryngeal cuffs during retrograde intubation procedures. This is because inflatable cuffs can potentially be punctured and deflated, which could result in lack of seal and problems with ventilation.

The tube is formed from a bendable plastics material that will be described in more detail below. With the exception of the region at the distal end of the tube where it starts to join the cuff, the external profile of the tube is substantially uniform between the distal end of the tube where it starts to meet the cuff and the proximal end of the tube. The term "substantially uniform" means that there is no region of the tube which could act as a buccal cavity stabiliser i.e. an expanded region extending on either side of the airway tube. Put another way, there is no section of the tube that extends on either side of the tube and which is generally broader in profile than the airway tube itself. The internal diameter of the airway tube will preferably be substantially uniform and circular, whether the tube has a circular or oval exterior profile, and the distal opening of the airway tube into the cuff is a single opening to help reduce the resistance to flow through the device.

Figures 4, 4A, 4B, 4C, 4D:
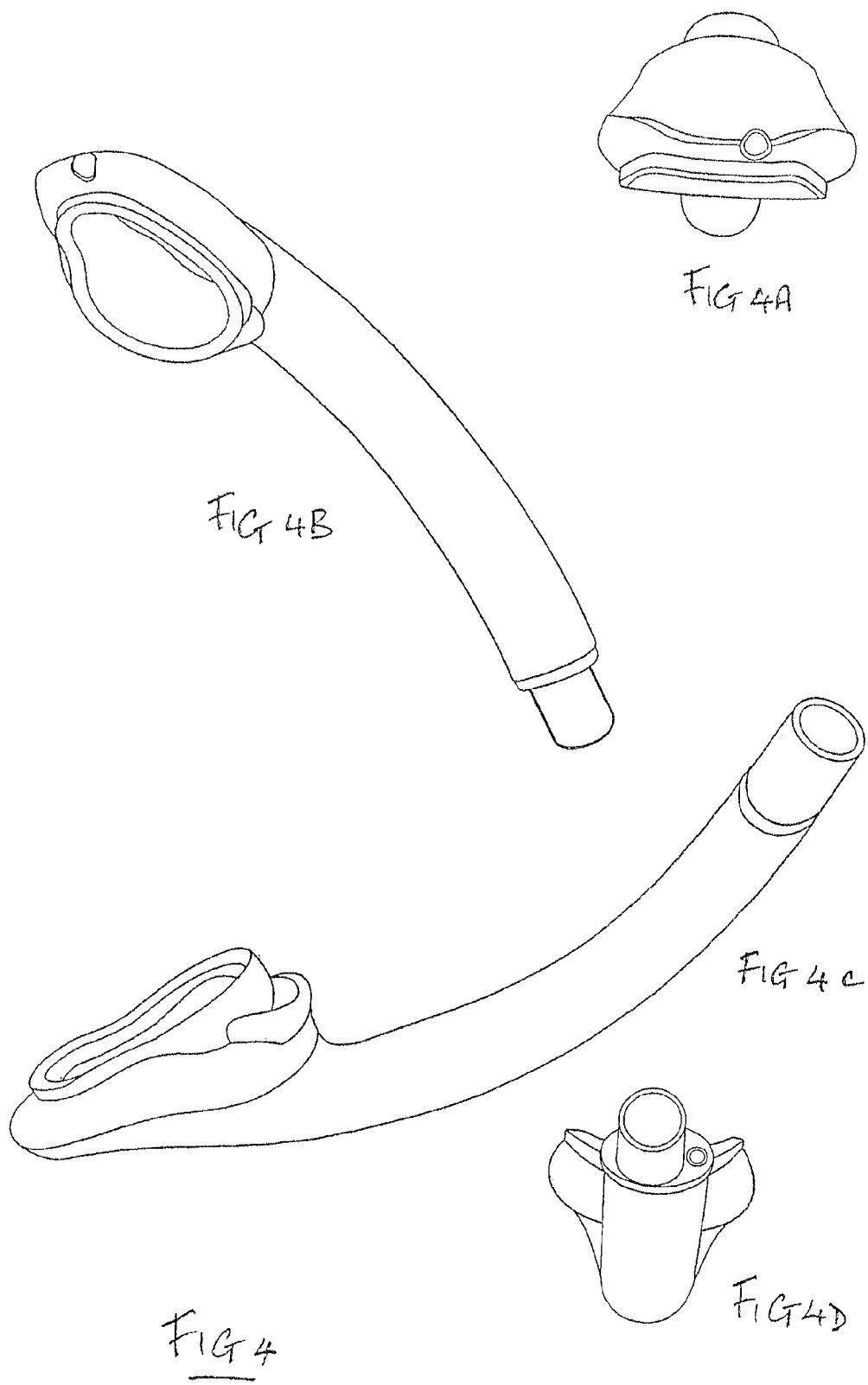
FIGS. 4-4D illustrate various perspective views of the embodiment shown in FIG. 3.

The airway tube can be formed with a variety of profiles. In the embodiment illustrated in FIGS. 1 and 2 the general external profile of the airway tube is substantially circular. This can be seen most clearly in FIG. 2D. In contrast, in the embodiment illustrated in FIGS. 3 and 4, the airway tube has a generally elliptical external profile, although the bore passing through the airway tube is substantially circular in cross-section. These are just two of many profiles that might be selected by the designer.

A connector 118 which fits into the end of the airway tube is shown in more detail in FIG. 10. There are two important features to note from this embodiment. Firstly, the length of the connector is significantly greater than a conventional connector and is such that it extends, in use, into the patient's mouth and beyond his/her teeth. In that way it acts as a bite protector and prevents the patient from inadvertently biting through the relatively soft material of the airway tube. The patient biting down onto the airway device and particularly or completely occluding airflow is a problem in certain procedures and with certain patients. Secondly, the connector fits into a recess formed within the airway tube by the moulding process. In this way, the internal surface of the airway tube 109 is substantially smooth and uniform. The internal diameter of the tube from the proximal opening in the connector to the distal end where it opens out into the cuff is substantially uniform. There is therefore no significant step change in internal diameter at the inner end of the connector, which leads to improved airflow and lower resistance to flow. This arrangement is shown particularly in FIG. 10C being a section along line E-E.

In addition to the airway tube, the embodiments shown in FIGS. 1 to 4 inclusive include a second passageway 40 that extends from an opening 42 in the distal end of the device to an opening 41 in the proximal end of the device. This second, gastric tube passageway, is designed to allow an operator to pass a gastric tube down into the stomach of a patient without interrupting anaesthesia, during EMS or during pre-hospital airway management. This second passageway also allows for detection of any gastric aspirate in the event of passive regurgitation during use. This second passageway must be large enough to allow a small bore gastric tube to pass easily through the device. Typically a gastric tube passageway would be between 6 to 14 French gauge diameter.

The gastric tube passageway 40 and 140 shown in FIGS. 1 and 3 is shown housed substantially within the body of the airway device. However, it is also possible that this passageway could run externally of the new main body, for example laterally or along the dorsal face of the device body.

Another feature of the passageways in these embodiments is that they are displaced to one side of the central longitudinal axis of the device, in this case to the right-hand side of the central longitudinal axis, as viewed from the open face of the cuff. However, the passageway, which is optional, could just as well exit along the mid-line or on the central longitudinal axis of the device as illustrated by 242 in FIG. 11.

A further embodiment is illustrated in FIG. 7. In this example a laryngeal cuff is formed around a pre-formed or pre-cut piece of airway tube. This has the cost advantage that the airway tube may be formed from relatively inexpensive PVC tube or the like with a connector in one end and the cuff moulded over the other end. Once again the airway tube may be circular in profile or elliptical or any other profile as selected by the designer.

Figures 6, 6A, 6B, 6C:
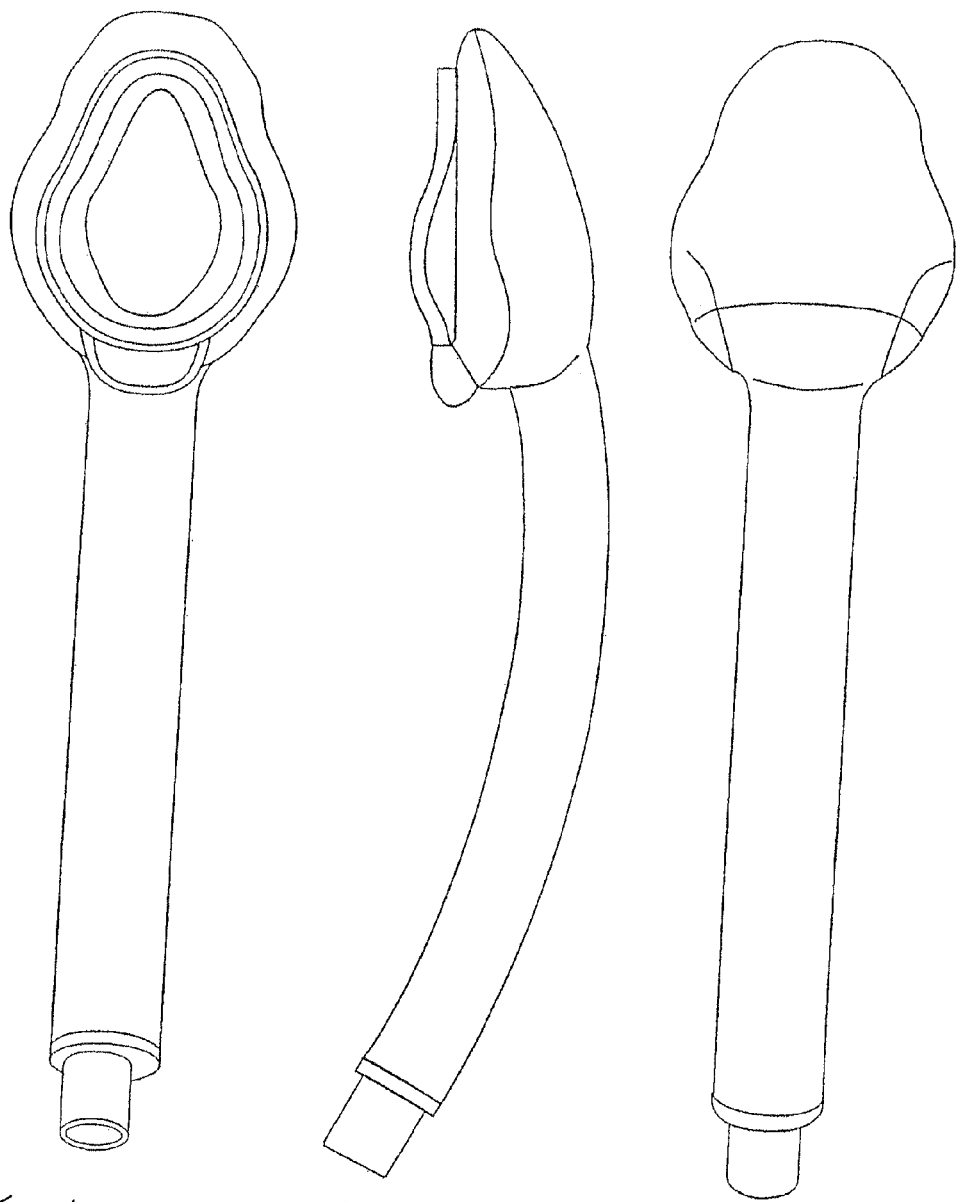
FIGS. 6-6C illustrate front, side and rear elevational views of an airway device according to a further embodiment of the present invention.

FIGS. 1B and 3B and 6B amongst others show the generally curvilinear shape of the device along its longitudinal axis. This shape is designed to correspond with the mouth/throat opening in an anaesthetized patient. Whilst the device is flexible it is resiliently deformable and tends to return to this concave/convex shape in its unstressed state.

In addition to passing tubes or other items through the gastric tube passageway, it is possible to pass items such as a guide wire directly into the trachea through the airway tube. To facilitate this the interior surface 150 of the cuff within the opening is ramped so as to direct a probe into the trachea (see FIG. 8C).

The device may be constructed from any suitable plastics material as selected by the materials specialist. Latex-free medical grade silicone rubber is one preferred material. The cuff should be soft in texture to avoid undue damage to the surrounding tissue. Other suitable materials for construction of this type of device include, but are not limited to, Poly Vinyl Chloride (PVC), Thermoplastic Elastomers such as the styrenic block copolymers (e.g. Styrene Butadiene Styrene (SBS), Styrene Ethylene Butylene Styrene (SEBS)), and Thermoplastic Olefin Blends (TPO), Thermoplastic Poly-Urethanes (TPU), Thermoplastic Vulcanisates (TPV), Copolyester (COPE), Polyether Block Amides (PEBAX), Melt Processable Rubbers, Flexible Co-polymers such as EVA, and foamed versions thereof, where appropriate.

A further important factor involved in the choice of a suitable material is transparency. Ideally the material or materials of construction should be substantially clear or transparent. This enables the anesthetist or operator to see the inner lumen of the airway to check for blockages or other problems. Such transparent materials are known to the materials specialist.

By way of a preferred softness (hardness) range, on the Shore A scale of Hardness, a hardness of less than 30 for the face of the cuff that contacts the laryngeal inlet is optimum. By way of a preferred range, a value on the same scale of between 0 to 20 is preferred, with a particularly preferred range of 0 to 5. The apparent softness of the cuff can be further adapted by forming cavities or channels within the body of the cuff itself.

In a further embodiment the cuff may be pre-filled with a fluid such as air, or other non-toxic gas, or a non-toxic liquid. In this context the term fluid has a broad meaning and includes any suitable gas, liquid, vapour or mixtures or combination thereof and will be determined and designed by an expert in this field of anatomy/anaesthesia in conjunction with the materials specialist. The cuff will be constructed of such a material which will not allow nitrous oxide (anaesthetic gas) to diffuse through the material to any significant amount so that the extra luminal pressure is kept constant. It follows therefore that the cuff should be substantially impermeable to the fluid with which is filled and to anaesthetic gases.

Alternatively, the cuff can be formed from a soft, foamed material or can be foam filled. In either case this provides a soft deformable but shaped surface around the face of the cuff to engage over the anatomy of the laryngeal inlet region. Such a foam filled device will minimise any potential damage to the structures in that region whilst still providing a substantially complete seal.

In the case of embodiments with a substantially circular airway tube and a gastric tube passageway which runs internally along the length of the device (as shown for example in FIGS. 1 and 2), the centre of the bore of the airway tube can be displaced to one side of the central or mid-line axis of the airway tube itself. This displacement provides space for the gastric tube passageway to run alongside the bore of the airway tube. This arrangement is shown most clearly in FIG. 2D. The gastric tube passageway is, in effect, housed within the outer body of the airway tube. This arrangement makes for a neat, streamlined appearance in comparison to the arrangement in which the gastric tube passageway is external to or mounted on the back of the device.

In terms of materials of manufacture and construction of an airway device according to the present invention, it is advantageous to form the front or open face of the cuff from a softer material than the remainder of the device. FIG. 1B shows a so-called "split line" 32 between the softer plastics material on the face of the cuff and slightly firmer material on the dorsal or back part of the cuff 19. The exact position of this split line may vary as determined by the designer. This line is shown in a slightly different position in FIG. 9, where it is shown as feature 132.

By moving this split line towards the dorsal face of the cuff, this ensures that the sides of the cuff 33, 34 are also made of the softer material. The sides are therefore more easily deformed which contributes significantly to the ease of insertion, and removal, of the cuff during use. The cuff squeezes and seals into the space above the laryngeal inlet, cupping the laryngeal inlet to create a good seal for ventilation. As the cuff reduces in width and squeezes into position, the airway opening increases in depth. This increase in depth reduces the likelihood of the epiglottis occluding the airway during ventilation, a problem with prior art devices.

Turning now to methods of manufacturing airway devices generally, and in particular airway devices according to the present invention and airway devices as described in GB2, 393,399A, several new and cost-effective methods have been devised. These include injection moulding the device as a single unit using a one-shot or a two-shot process. Such methods also include extruding an airway tube and injection moulding a cuff around the tube in a one-shot or two-shot process.

It follows therefore that the airway tube may be manufactured by extrusion or injection moulding and the cuff portion may be formed by one-shot or two-shot injection moulding.

Accordingly, one method of making an airway device according to the present invention is to provide a mould, the mould including interior walls which define the shape of the airway device, and injecting into said mould a molten thermoplastic compound. Once cooled the item is ejected from the mould. In a further embodiment a two-shot process is used in which molten thermoplastic compound of a first hardness is first injected into the mould, which is retained in a pre-determined position such that only a pre-determined portion of the mould is filled with polymeric material. A second molten thermoplastic compound is then injected into the remaining space in the mould to complete the injection moulding process. In this manner the relatively firmer airway tube and dorsal portion of the cuff can be formed first and the relatively softer face of the cuff can be formed in the second part of the operation. Alternatively the face of the cuff can be formed first and the remainder of the device is formed in the second part of the operation.

In an alternative method an airway tube is formed in a first step, either by extrusion or cutting a pre-determined length from a longer length of tubing. A mould defining a hollow space which will become the cuff region in the finished product is then placed around the airway tube and thermosetting plastic is injected into the mould in a one-step or a two-step process.

In a third manufacturing embodiment a mould defining the cuff region is used to produce a cuff by either a one-step or a two-step injection moulding process. The cuff produced from this mould includes a recess adapted to accept an airway tube. In a separate operation or operations an airway tube is formed by extrusion or in some other manner. The airway tube is then inserted into and bonded to the recess provided in the cuff for that purpose.

According to a further method of manufacture, the moulding process may be used to mould not only the laryngeal cuff on to the end of a pre-formed airway tube, but also a soft coating over the airway tube itself. Whiles this requires a larger mould, and more plastics material, it has the advantage that the finished device has a uniform finish over substantially the whole of its outer surface. It is softer for the patient and more aesthetically appealing for the operator. Having a pre-formed airway tube running most of the length of the device gives a degree of resilience and rigidity which is particularly helpful when using very soft plastics material.

In terms of plastics materials used in these methods of manufacture, these will be determined by the materials specialist and are generally only limited by the ability to bond the chosen materials together. By way of example only, typically PVC can be used to mould the airway tube, the whole of the cuff region, the dorsal portion of the cuff region or any seals between these components. Polyolefins such as polyethylene and polypropylene or a polyurethane can be used to form the airway tube and/or the dorsal portion of the cuff region. A thermoplastic elastomer or a silicone rubber can be used to form the airway tube, the face of the cuff, the dorsal portion of the cuff, the whole of the cuff and any secondary seals therebetween.

In this context the term "bond" has a particularly broad meaning. It encompasses any method or process in which two or more parts are permanently joined together. It includes, but is in no way limited to, molecular bonding, glueing using chemical adhesives, welding, including ultrasonic welding. The preferred method or methods of bonding will be selected by the materials specialist in this area.

The invention claimed is:

1. An airway device for human or animal use comprising an airway tube having a distal end and a proximal end, the distal end of which is surrounded by a laryngeal cuff, wherein the cuff is non-inflatable and is pre-formed in a shape such that a face region of the cuff is adapted to fit snugly over the laryngeal inlet of a patient, the face of the laryngeal cuff region being preformed from a soft deformable material and shaped to form an anatomical fit over the laryngeal inlet of a patient and which incorporates protuberances that form a good seal with the laryngeal framework of the patient, and wherein the external profile of the tube is substantially uniform between the distal end of the tube where it starts to meet the cuff and the proximal end of the tube, and wherein the face region of the cuff is formed from a material with a Shore hardness on the A scale of less than 30.

2. An airway device as claimed in claim 1 wherein the face region of the cuff is formed from a material of Shore hardness on the A scale of between 0 and 20.

3. An airway device as claimed in claim 1 wherein the cuff is formed from a material of Shore hardness on the A scale of between 0 and 5.

4. An airway device as claimed in claim 1 wherein the profile of the airway tube is substantially circular.

5. An airway device as claimed in claim 1 wherein the profile of the airway tube is substantially elliptical.

6. An airway device as claimed in claim 1 wherein the device further comprises a gastric tube passageway extending from the proximal end of the airway tube to the distal end of the cuff.

7. An airway device as claimed in claim 6 wherein the gastric tube passageway is housed substantially within the body of the device.

8. An airway device according to claim 6 wherein the distal end exit of the gastric tube passageway exits the cuff centrally, that is along the line of the central longitudinal axis of the device.

9. An airway device according to claim 6 wherein the distal end exit of the gastric tube passageway is displaced to one side of the central longitudinal axis of the device.

10. A device according to claim 1 wherein the device further comprises one or more flexible flanges extending around the opening in the face region of the cuff.

11. A device according to claim 10 wherein the flexible flanges extend substantially around the entire circumference of the opening in the cuff.

12. A device according to claim 10 wherein a plurality of flanges are provided said flanges being spaced apart radially around the opening one from another such that the flanges are substantially concentric.

13. A device according to claim 1 wherein said device further comprises a connector adapted to connect the proximal end of the airway tube to a gas supply.

14. A device according to claim 13 wherein said connector extends into said airway tube and at least part way along the length of said airway tube to act as a bite protector to prevent a patient from constricting the airway tube by biting on it.

15. A device as claimed in claim 13 wherein said connector fits into an internal annular recess at the proximal end of the airway tube such that the diameter, or internal cross-section of the airway tube where the tube is non-circular internally, remains substantially constant along the length of the tube when the connector is in place.

16. An airway device according to claim 15 wherein the distal end of the connector abuts in use a shoulder in the airway tube to prevent the connector from passing into the airway tube beyond a certain point.

17. An airway device according to claim 1 wherein the face of the laryngeal cuff is adapted to form an anatomical fit over the laryngeal inlet of a patient incorporates protuberances designed to form a good seal with the pyriform fossae and aryepiglottic folds of the laryngeal inlet of the patient.

18. An airway device according to claim 17 wherein the face of the laryngeal cuff adapted to form an anatomical fit over the laryngeal inlet of a patient incorporates protuberances designed to form a good seal with the valleculae, epiglottis, aryepiglottic folds, pyriform fossae and around the thyroid & cricoid cartilages.

19. An airway device according to claim 1 wherein the face of the laryngeal cuff adapted to fit anatomically over the laryngeal framework of a patient incorporates grooves designed to allow passage of vital arteries, veins and nerves supplying the laryngeal framework.

20. An airway device according to claim 1 wherein the distal tip of the laryngeal cuff is so sized and shaped as to remain above the upper oesophageal sphincter in use.

21. An airway device according to claim 20 wherein the distal tip of the laryngeal cuff is substantially concave in shape.

22. An airway device as claimed in claim 1 wherein the face of the laryngeal cuff and the airway tube are formed from material of substantially the same Shore hardness.

23. An airway device as claimed in claim 1 wherein the face of the laryngeal cuff and the airway tube are formed from materials of different Shore hardness.

24. An airway device as claimed in claim 1 wherein the airway tube together with the back or dorsal part of the cuff are made from material of one Shore hardness and the face of the cuff is made from a material of a different Shore hardness, such that the face of the cuff is made of a softer material than the airway tube and the back or dorsal part of the cuff.

* * * * *